(12) United States Patent
Yokoyama

(10) Patent No.: US 10,617,466 B2
(45) Date of Patent: Apr. 14, 2020

(54) TREATMENT INSTRUMENT AND TREATMENT SYSTEM

(71) Applicant: OLYMPUS CORPORATION, Hachioji-shi, Tokyo (JP)

(72) Inventor: Ken Yokoyama, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 312 days.

(21) Appl. No.: 15/644,316

(22) Filed: Jul. 7, 2017

(65) Prior Publication Data

US 2017/0303992 A1     Oct. 26, 2017

Related U.S. Application Data

(63) Continuation of application No. PCT/JP2015/071132, filed on Jul. 24, 2015.

(30) Foreign Application Priority Data

Jan. 7, 2015  (JP) .................................. 2015-001838

(51) Int. Cl.
*A61B 18/12* (2006.01)
*A61B 18/14* (2006.01)
(Continued)

(52) U.S. Cl.
CPC ........ *A61B 18/148* (2013.01); *A61B 1/00114* (2013.01); *A61B 1/00124* (2013.01);
(Continued)

(58) Field of Classification Search
CPC .... A61B 17/320016; A61B 17/320068; A61B 18/1206; A61B 18/148;
(Continued)

(56) References Cited

U.S. PATENT DOCUMENTS 4,886,060 A     12/1989  Wiksell
5,630,813 A      5/1997  Kieturakis
(Continued)

FOREIGN PATENT DOCUMENTS

JP      H06-292685 A     10/1994
JP      H07-95985 A       4/1995
(Continued)

OTHER PUBLICATIONS

May 28, 2018 Extended European Search Report issued in European Patent Application No. 15876904.2.
(Continued)

*Primary Examiner* — Daniel W Fowler
(74) *Attorney, Agent, or Firm* — Oliff PLC

(57) ABSTRACT

A treatment instrument which is used under an environment filled with an electrically conductive liquid includes a probe, a hollow sheath and an insulating member. The probe has a distal portion to chip a treatment target part by ultrasonic vibration and which allows the distal portion to function as one pole in a bipolar electrode. The sheath surrounds the probe. The insulating member covers the sheath except for a partial region on the distal side of the sheath. The partial region on the distal side of the sheath functions as the other pole in the bipolar electrode.

12 Claims, 15 Drawing Sheets

(51) Int. Cl.
*A61B 18/00* (2006.01)
*A61B 17/16* (2006.01)
*A61B 1/317* (2006.01)
*A61B 1/00* (2006.01)
*A61B 17/32* (2006.01)
*A61N 7/02* (2006.01)
*A61B 17/00* (2006.01)

(52) U.S. Cl.
CPC .............. *A61B 1/317* (2013.01); *A61B 17/16* (2013.01); *A61B 17/320016* (2013.01); *A61B 17/320068* (2013.01); *A61B 18/00* (2013.01); *A61B 18/1206* (2013.01); *A61N 7/02* (2013.01); *A61B 2017/00862* (2013.01); *A61B 2017/320069* (2017.08); *A61B 2017/320071* (2017.08); *A61B 2017/320088* (2013.01); *A61B 2017/320089* (2017.08); *A61B 2018/00083* (2013.01); *A61B 2018/00107* (2013.01); *A61B 2018/00565* (2013.01); *A61B 2018/00595* (2013.01); *A61B 2018/00607* (2013.01); *A61B 2018/00982* (2013.01); *A61B 2018/00994* (2013.01); *A61B 2018/126* (2013.01); *A61B 2018/1472* (2013.01); *A61B 2018/1497* (2013.01)

(58) Field of Classification Search
CPC ......... A61B 2017/00862; A61B 2017/320069; A61B 2017/320071; A61B 2017/320088; A61B 2017/320089; A61B 2018/00083; A61B 2018/00107; A61B 2018/00565; A61B 2018/00595; A61B 2018/00607; A61B 2018/00982; A61B 2018/00994; A61B 2018/126; A61B 2018/1472
See application file for complete search history.

(56) References Cited

U.S. PATENT DOCUMENTS

| | | | |
|---|---|---|---|
| 5,904,681 A | 5/1999 | West, Jr. | |
| 6,293,945 B1* | 9/2001 | Parins | A61B 18/1402 606/45 |
| 2002/0007200 A1* | 1/2002 | Desinger | A61B 17/320068 607/96 |
| 2002/0035364 A1* | 3/2002 | Schoenman | A61B 18/1402 606/45 |
| 2003/0073987 A1 | 4/2003 | Sakurai et al. | |
| 2003/0084907 A1 | 5/2003 | Pacek et al. | |
| 2003/0163131 A1 | 8/2003 | Manna et al. | |
| 2004/0147945 A1* | 7/2004 | Fritzsch | A61B 17/320016 606/169 |
| 2005/0027235 A1* | 2/2005 | Knudsen | A61B 18/148 604/20 |
| 2005/0101945 A1 | 5/2005 | Sakurai et al. | |
| 2008/0058803 A1* | 3/2008 | Kimura | A61B 17/320068 606/49 |
| 2009/0023986 A1 | 1/2009 | Stewart et al. | |
| 2010/0191173 A1 | 7/2010 | Kimura et al. | |
| 2013/0345515 A1 | 12/2013 | Fitzmaurice | |
| 2014/0135804 A1 | 5/2014 | Weisenburgh, II et al. | |
| 2014/0324084 A1 | 10/2014 | Sanai et al. | |

FOREIGN PATENT DOCUMENTS

| | | |
|---|---|---|
| JP | 2959779 B2 | 10/1999 |
| JP | 2001-511043 A | 8/2001 |
| JP | 2002-177287 A | 6/2002 |
| JP | 2003-116870 A | 4/2003 |
| JP | 2003-126110 A | 5/2003 |
| JP | 2005-152098 A | 6/2005 |
| JP | 2005-518864 A | 6/2005 |
| JP | 2008-55151 A | 3/2008 |
| WO | 2014/045687 A1 | 3/2014 |

OTHER PUBLICATIONS

May 28, 2018 Extended European Search Report issued in European Patent Application No. 15876902.6.
Jun. 6, 2018 Extended European Search Report issued in European Patent Application No. 15876903.4.
Oct. 20, 2015 International Search Report issued in International Patent Application No. PCT/JP2015/071134.
Mar. 21, 2017 Office Action issued in Japanese Patent Application No. 2016-568264.
Feb. 21, 2017 Office Action issued in Japanese Patent Application No. 2016-568266.
U.S. Appl. No. 15/644,604, filed Jul. 7, 2017 in the name of Yokoyama.
Oct. 27, 2015 International Search Report issued in International Patent Application No. PCT/JP2015/071132.
Oct. 27, 2015 International Search Report issued in International Patent Application No. PCT/JP2015/071133.
U.S. Appl. No. 15/644,565, filed Jul. 7, 2017 in the name of Yokoyama.
Dec. 24, 2018 Office Action issued in Chinese Patent Application No. 201580072850.5.
Dec. 27, 2018 Office Action issued in Chinese Patent Application No. 201580072822.3.
Dec. 25, 2018 Office Action issued in Chinese Patent Application No. 201580072777.1.
Jul. 11, 2017 International Preliminary Report on Patentability issued in International Patent Application No. PCT/JP2015/071133.
Jul. 11, 2017 International Preliminary Report on Patentability issued in International Patent Application No. PCT/JP2015/071132.
Jul. 11, 2017 International Preliminary Report on Patentability issued in International Patent Application No. PCT/JP2015/071134.
Nov. 1, 2018 Office Action issued in U.S. Appl. No. 15/644,565.
May 18, 2018 Office Action issued in U.S. Appl. No. 15/644,565.
Sep. 10, 2019 Office Action issued in U.S. Appl. No. 15/644,604.
Jan. 13, 2020 Office Action issued in U.S. Appl. No. 15/644,604.

* cited by examiner

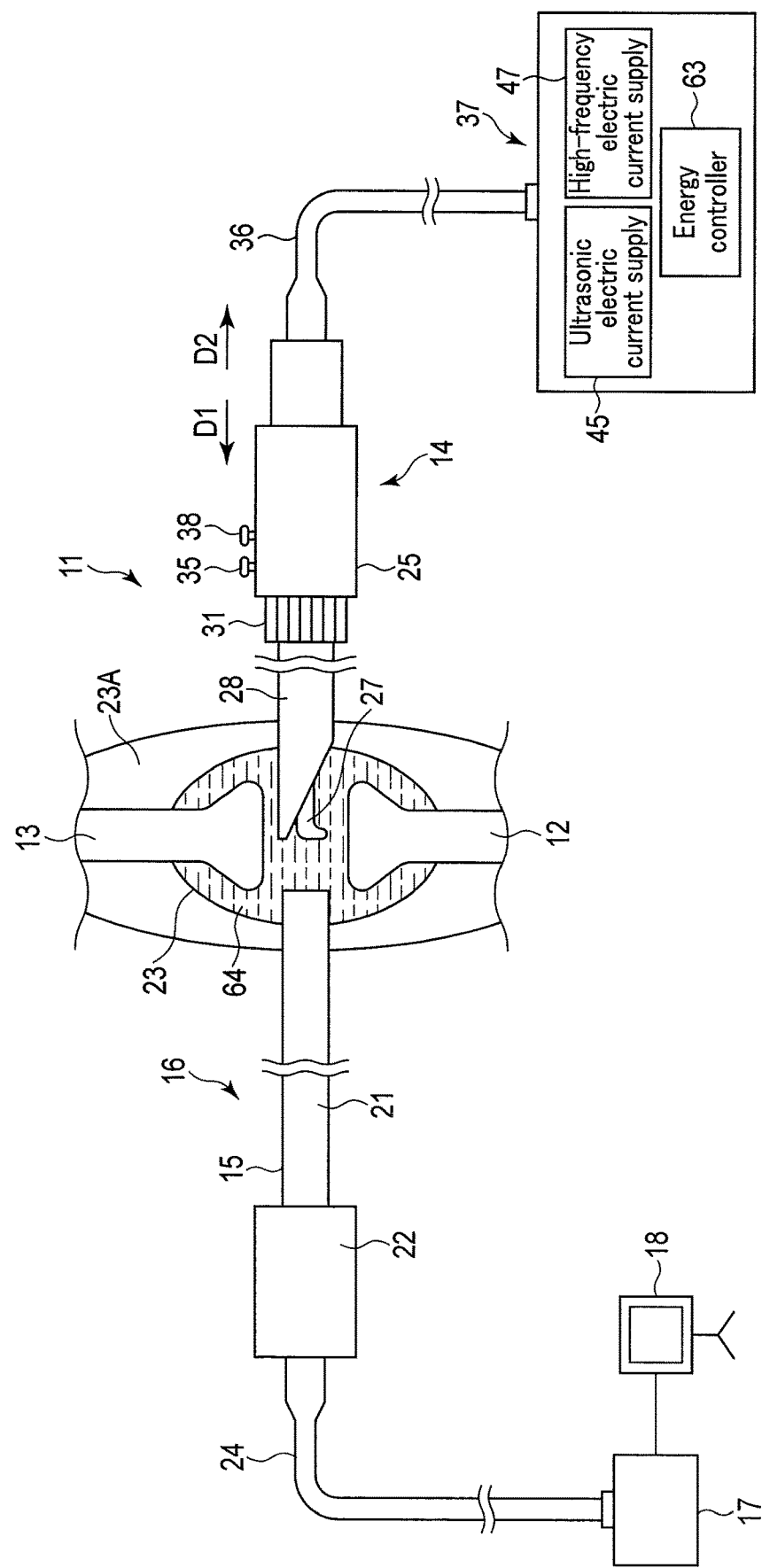
F I G. 1

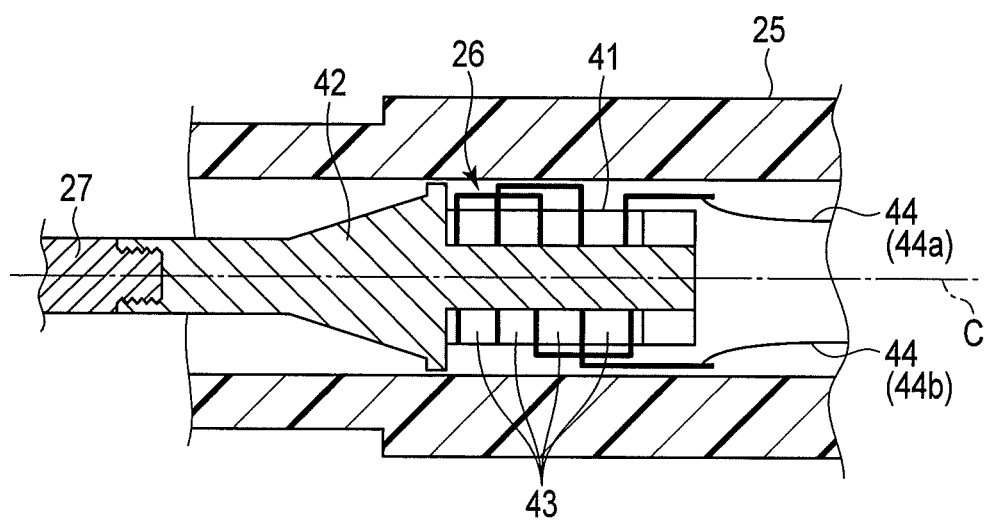
F I G. 3

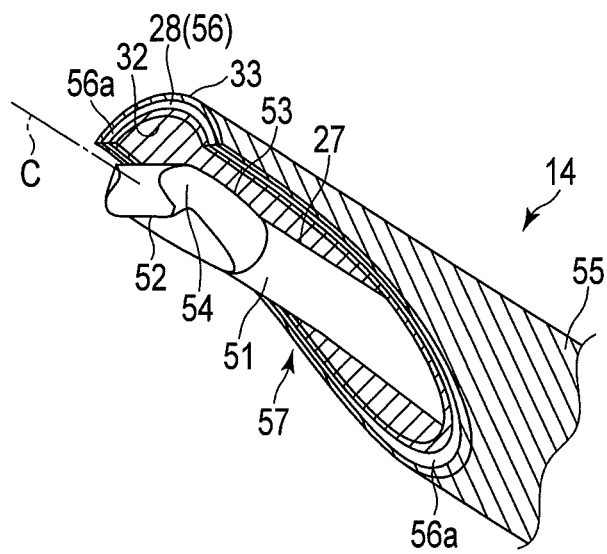
F I G. 7A
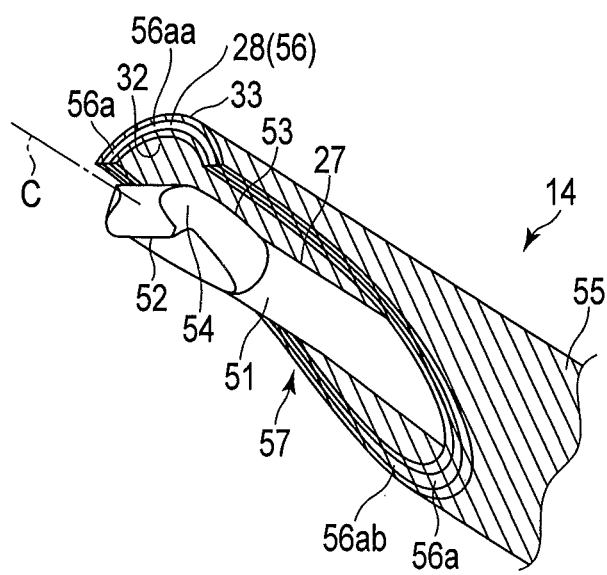
F I G. 7B

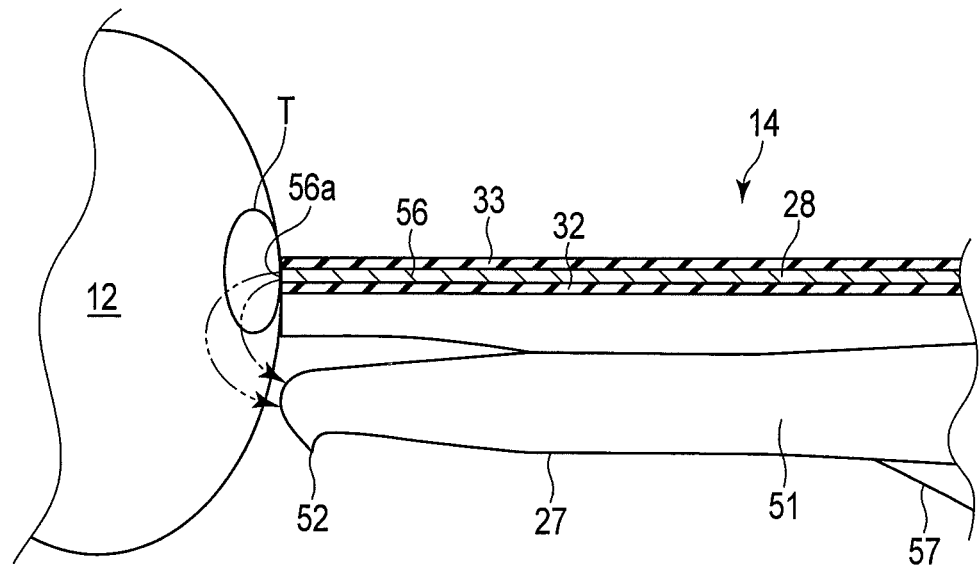
F I G. 10
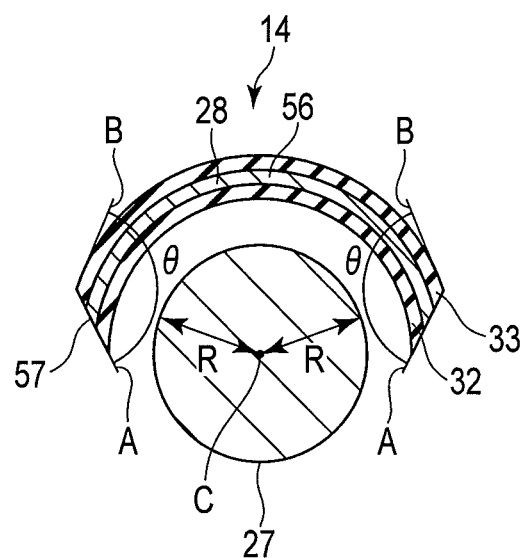
F I G. 11

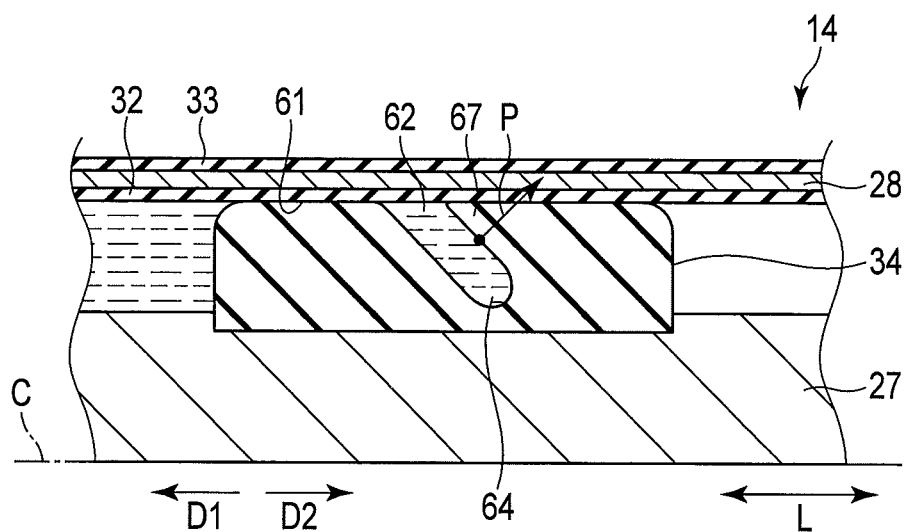
F I G. 13
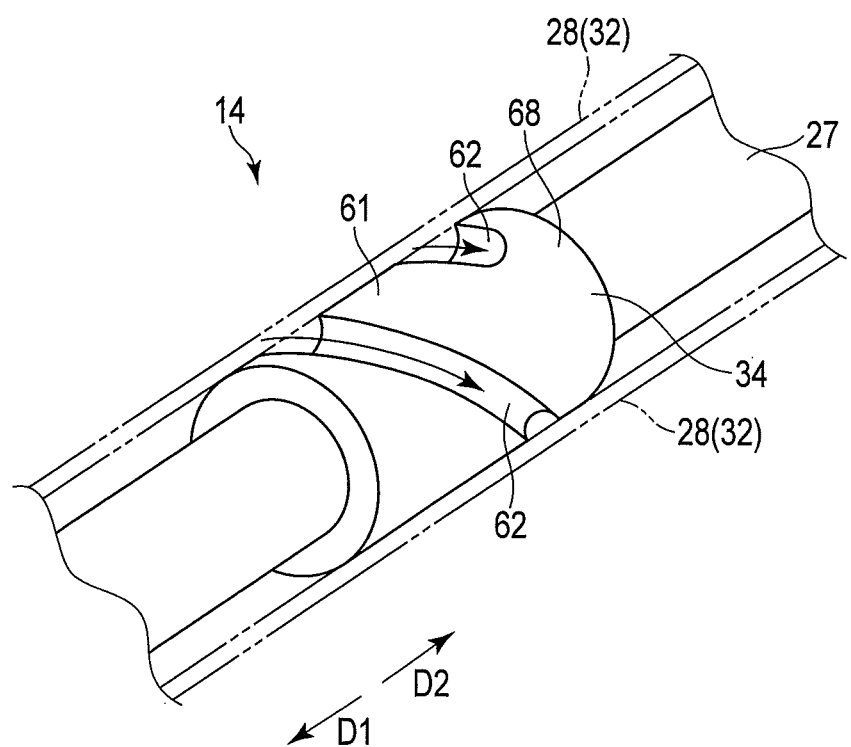
F I G. 14

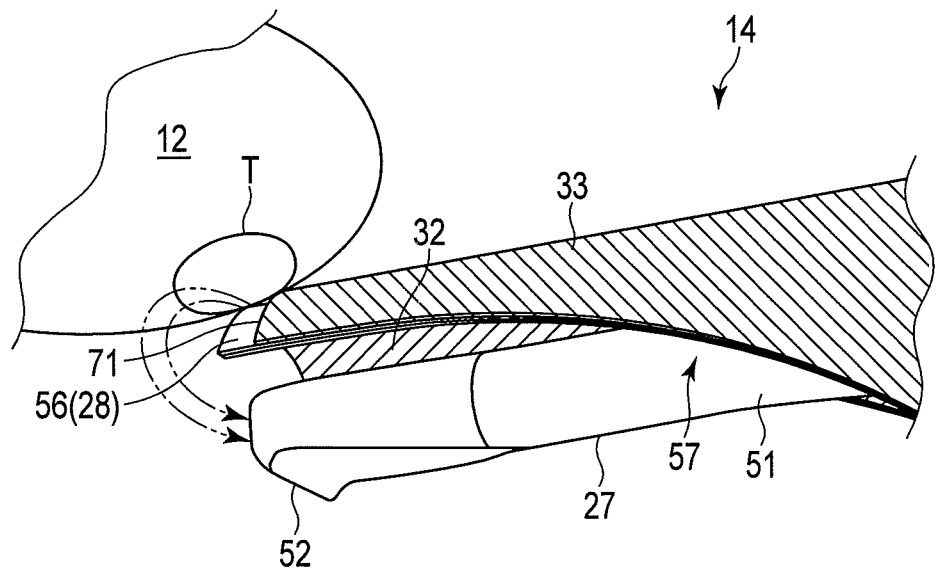
F I G. 17
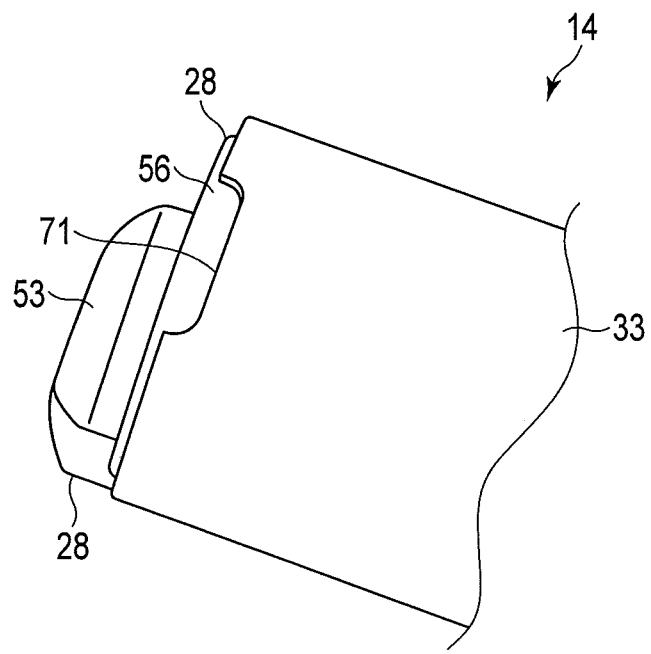
F I G. 18

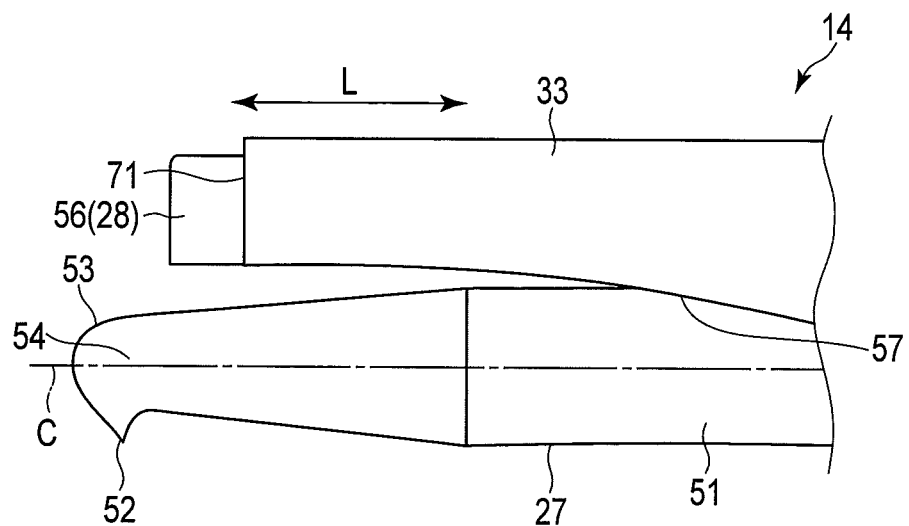
F I G. 19
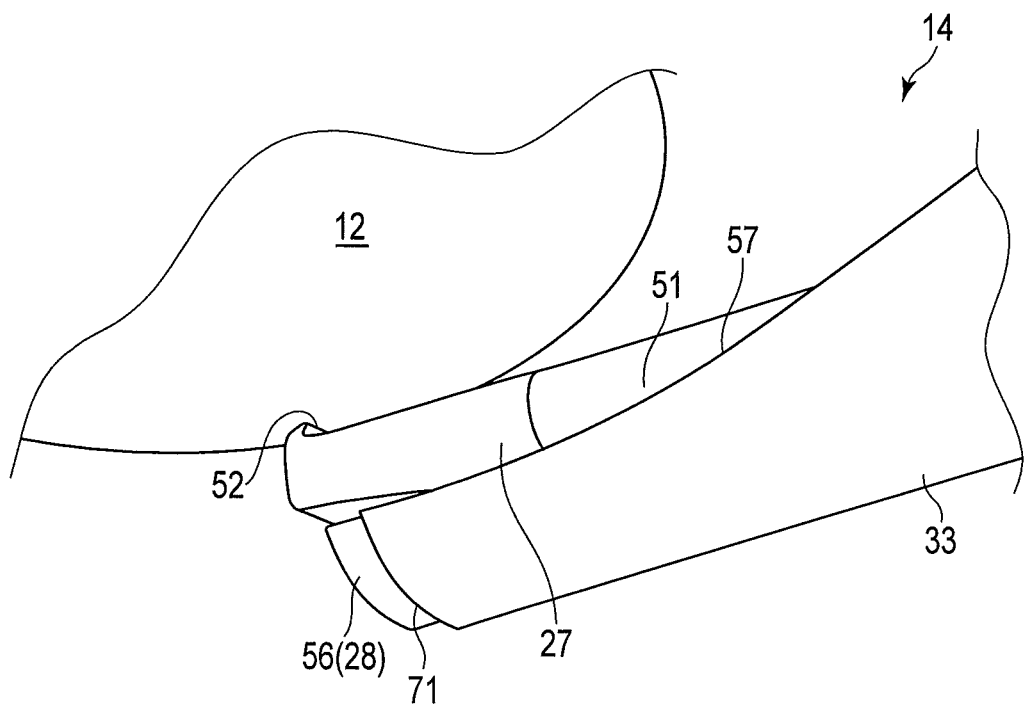
F I G. 20

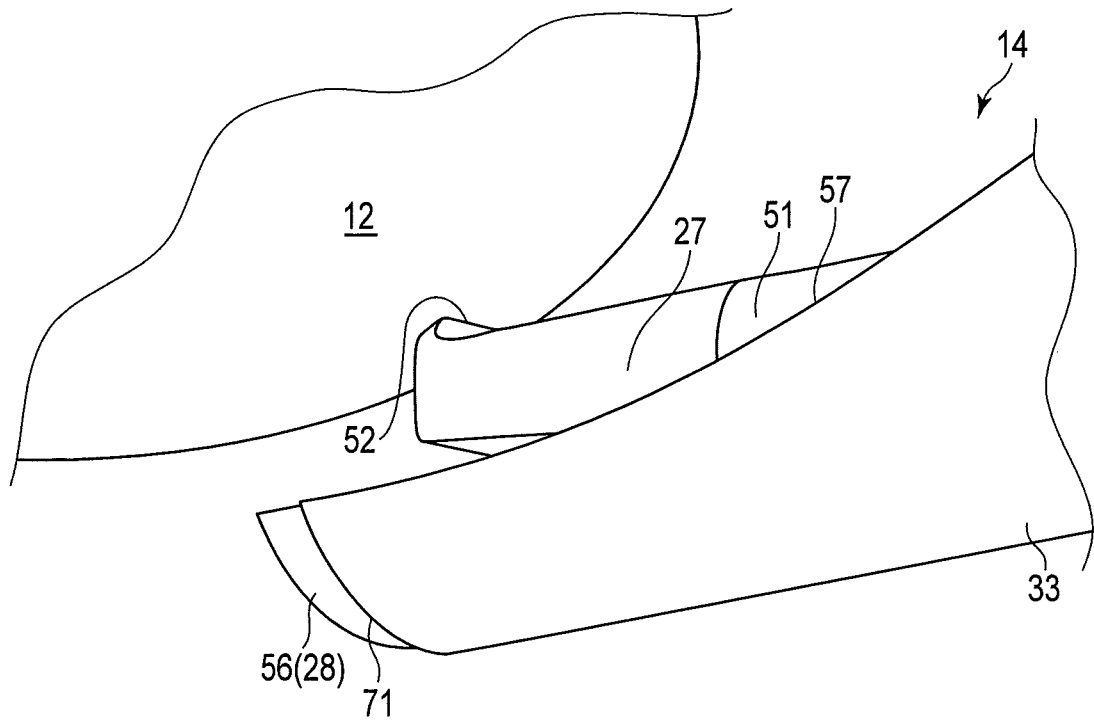
F I G. 23
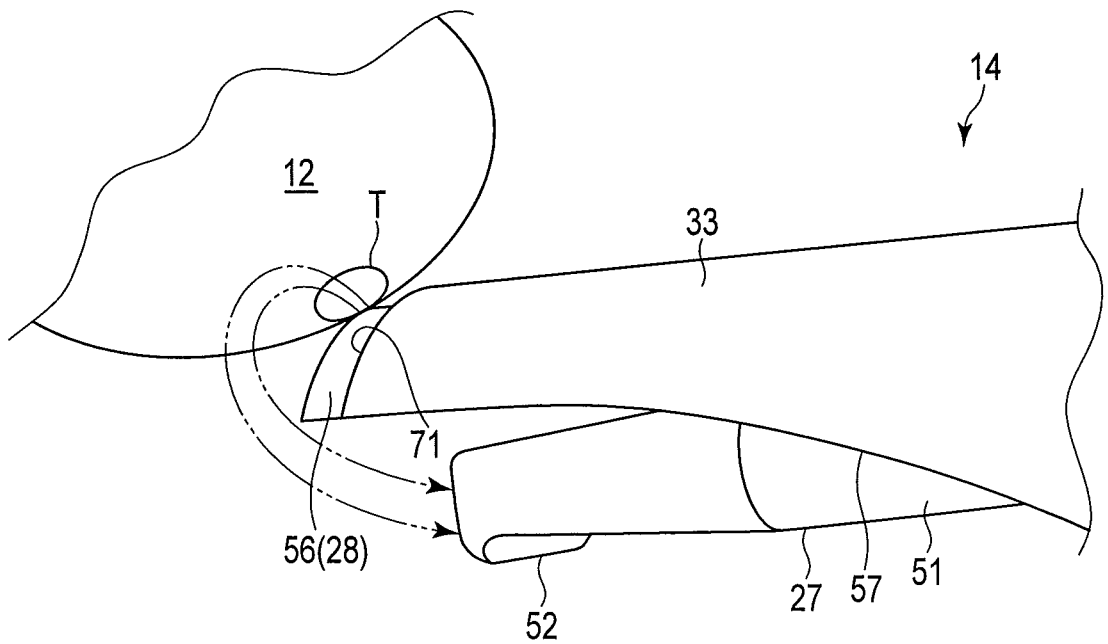
F I G. 24

TREATMENT INSTRUMENT AND TREATMENT SYSTEM

CROSS-REFERENCE TO RELATED APPLICATIONS

This application is a Continuation Application of PCT Application No. PCT/JP2015/071132, filed Jul. 24, 2015 and based upon and claiming the benefit of priority from prior Japanese Patent Application No. 2015-001838, filed Jan. 7, 2015, the entire contents of all of which are incorporated herein by reference.

BACKGROUND OF THE INVENTION

1. Field of the Invention

The present invention relates to a treatment instrument for use in arthroscopic surgery. The present invention also relates to a treatment system comprising this treatment instrument.

2. Description of the Related Art

An ultrasonic surgical instrument to treat a hard tissue such as a bone by ultrasonic vibration has heretofore been known. For example, an ultrasonic handpiece disclosed in Jpn. Pat. Appln. KOKAI Publication No. 2005-152098 comprises an ultrasonic vibration mechanism which outputs ultrasonic vibration, and a horn which chips a hard tissue such as a bone by the vibration transmitted from the ultrasonic vibration mechanism. The horn has a body portion and a scalpel portion, and the scalpel portion abuts on and thus chips a hard tissue such as a bone.

BRIEF SUMMARY OF THE INVENTION

According to one aspect of the present invention, a treatment instrument which is used under an environment filled with an electrically conductive liquid is provided. The treatment instrument comprises a probe which has a distal portion to chip a treatment target part by ultrasonic vibration and which allows the distal portion to function as one pole in a bipolar electrode, a hollow sheath which surrounds the probe, and an insulating member which covers the sheath except for a partial region on the distal side of the sheath, wherein the partial region functions as the other pole in the bipolar electrode.

According to another aspect of the present invention, a treatment system comprising a treatment instrument according to the above treatment instrument and an endoscope apparatus to visualize a part to be treated with the treatment instrument is provided.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing a treatment system according to a first embodiment of the present invention;

FIG. 3 is a sectional view showing a vibration generator of the treatment instrument shown in FIG. 2 in a plane cut along a longitudinal direction of a probe;

FIG. 7A is a perspective view showing the probe and the sheath shown in FIG. 4 from an oblique direction;

FIG. 7B is a perspective view showing the probe and the sheath according to a modification from the oblique direction;

FIG. 10 is a side view showing a state where the treatment instrument shown in FIG. 1 is used to conduct a blood stanching treatment, and showing the internal probe by breaking the sheath along an extending direction of the probe;

FIG. 11 is a sectional view showing the sheath and the probe according to a first modification of the treatment system in the first embodiment cut in a plane that intersects (at right angles) with the extending direction of the probe;

FIG. 13 is a sectional view showing the seal member, the sheath, and the probe according to a third modification of the first embodiment cut in a plane along the extending direction of the probe;

FIG. 14 is a perspective view showing the seal member and the probe according to a fourth modification of the first embodiment;

FIG. 17 is a perspective view showing a state where the treatment instrument shown in FIG. 15 is used to conduct a blood stanching treatment;

FIG. 18 is a perspective view showing parts around the sheath, a second insulating member, and the probe according to a first modification of the treatment system in the second embodiment;

FIG. 19 is a side view showing parts in the vicinity of the probe and a distal portion of the sheath of a treatment portion of a treatment system according to a third embodiment;

FIG. 20 is a perspective view showing a state where the treatment instrument shown in FIG. 19 is used to conduct a treatment to chip a bone;

FIG. 23 is a perspective view showing a state where the treatment instrument shown in FIG. 22 is used to conduct the treatment to chip the bone; and FIG. 24 is a perspective view showing a state where the treatment instrument shown in FIG. 22 is used to conduct a blood stanching treatment.

DETAILED DESCRIPTION OF THE INVENTION

[First Embodiment]

Figure 2:
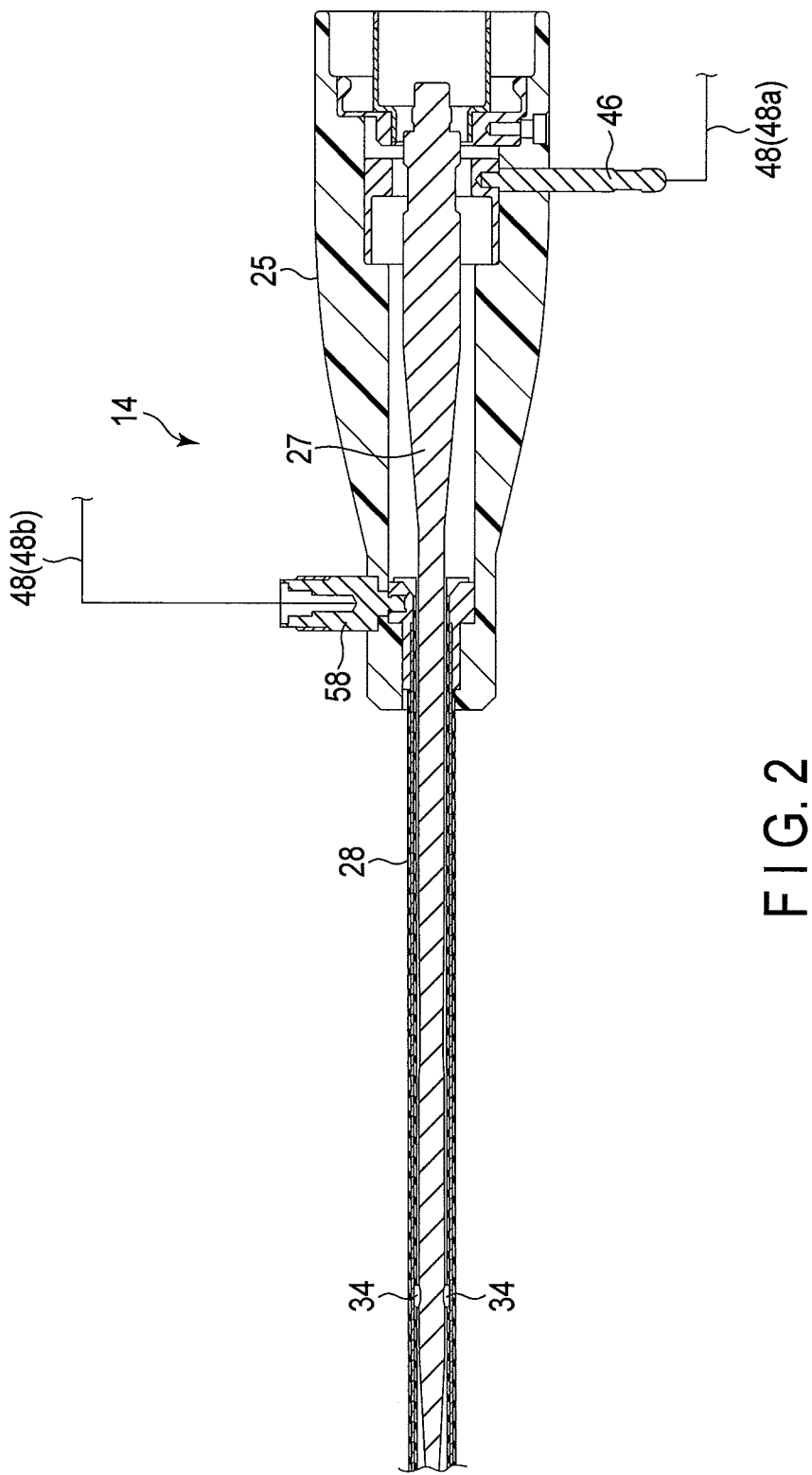
FIG. 2 is a sectional view showing in a plane cut along a longitudinal direction of a treatment instrument of the treatment system shown in FIG. 1.

A first embodiment of the present invention is described with reference to FIG. 1 to FIG. 10. A treatment system 11 is used in a treatment of joints of, for example, shoulders, knees, or elbows as treatment target parts. More specifically, as shown in FIG. 1, the treatment system 11 is used in a treatment of a part between a first bone 12 and a second bone 13 in a joint. The treatment system 11 comprises a treatment instrument 14, an electric supply unit 37 to actuate the treatment instrument 14, and an endoscope apparatus 16 including an arthroscope 15.

As shown in FIG. 1, the endoscope apparatus 16 comprises the arthroscope 15, an image processing unit 17, and a display unit 18.

The arthroscope 15 comprises an insertion portion 21 and a holding portion 22. In a treatment using the treatment system 11, a distal portion of the insertion portion 21 is inserted into an articular cavity 23. One end of a universal cord 24 is connected to the holding portion 22. The other end of the universal cord 24 is connected to the image processing unit 17 which is an image processor or the like. The image processing unit 17 is electrically connected to the display unit 18 which is a monitor or the like.

An imaging element is provided in the distal portion of the insertion portion 21. The imaging element images a subject through an observation window. The imaging element is electrically connected to the image processing unit 17 via an imaging cable extending through the insertion portion 21, the holding portion 22, and the universal cord 24. An imaged subject figure is subjected to image processing by the image processing unit 17. The subject figure which has been subjected to the image processing is then displayed on the display unit 18. An unshown light source unit is connected to the arthroscope 15, and light emitted from the light source unit is applied to the subject.

As shown in FIG. 1 to FIG. 4, the treatment instrument 14 comprises a holding portion 25 which constitutes an outer envelope, a vibration generator 26 (transducer) housed in the holding portion 25, a rod-shaped probe 27 connected to the vibration generator 26, a hollow (circular cylindrical) sheath 28 which covers the periphery of the probe 27 to protect the probe 27, a knob 31 (rotational knob) rotatably fixed to the holding portion 25, a first insulating member 32 which covers the inner peripheral surface of the sheath 28, a second insulating member 33 which covers the outer peripheral surface of the sheath 28, a seal member 34 provided between the probe 27 and the first insulating member 32, and energy input buttons 35 and 38 provided in the holding portion 25.

The explanation is provided below so that an arrow D1 shown in FIG. 1 is a distal direction of the probe 27 and an arrow D2 is a proximal direction of the probe 27.

To the holding portion 25, one end of a cable 36 is connected. The other end of the cable 36 is connected to the electric supply unit 37. The knob 31 is attached to the holding portion 25 rotatably around a central axis C of the probe 27. This knob 31 is linked to the probe 27 via an unshown link mechanism. Thus, it is possible to integrally rotate the probe 27 around the central axis C by rotating the knob 31 to the holding portion 25. This permits a surgeon to rotate the probe 27 around the central axis C during surgery.

For example, two energy input buttons 35 are provided in the holding portion 25. The number of the energy input buttons 35 is not exclusively two, and may be three or more or may be one. The surgeon can apply first energy (ultrasonic vibration) to a bone tissue (tissue) of a treatment target via the probe 27 by operating the first energy input buttons 35. The surgeon can also apply second energy (high-frequency electric current) to the bone tissue (tissue) of the treatment target via the sheath 28 by operating the second energy input button 38.

As shown in FIG. 3, the vibration generator 26 comprises an ultrasonic vibrator 41 and a horn member 42. The ultrasonic vibrator 41 is provided with (in the present embodiment, for example, four) piezoelectric elements 43 which change an electric current into ultrasonic vibration. One end of each of first electric wiring lines 44 (44a and 44b) is connected to the ultrasonic vibrator 41. The first electric wiring lines 44 (44a and 44b) are connected at the other ends to an ultrasonic electric current supply 45 of the electric supply unit 37 through the cable 36. When electric power is supplied to the ultrasonic vibrator 41 from the ultrasonic electric current supply 45 via the first electric wiring lines 44 (44a and 44b), ultrasonic vibration is generated in the ultrasonic vibrator 41. The first electric wiring line 44a is connected to a positive side of the ultrasonic electric current supply 45, and the first electric wiring line 44b is connected to a negative side of the ultrasonic electric current supply 45.

The ultrasonic vibrator 41 is attached to the horn member 42. The horn member 42 is made of a metallic material. The horn member 42 is provided with a substantially conical section changing portion which decreases in sectional area toward the distal direction of the probe 27. The ultrasonic vibration generated in the ultrasonic vibrator 41 is transmitted to the horn member 42, and the amplitude of the ultrasonic vibration is increased by the section changing portion.

Figure 4:
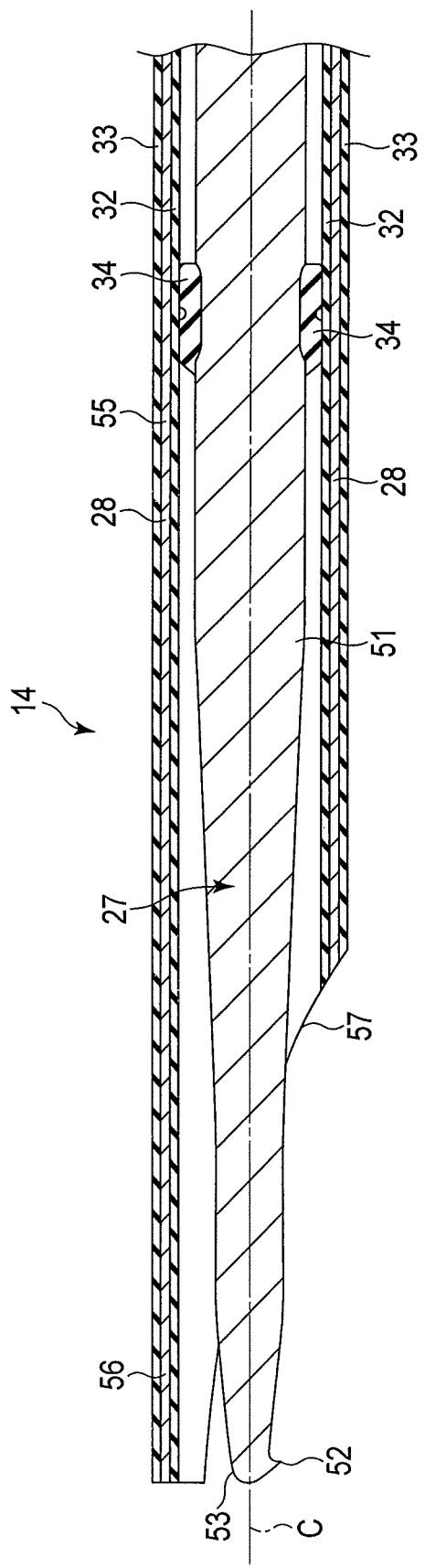
FIG. 4 is a sectional view showing the probe, a sheath, and a seal member of the treatment instrument shown in FIG. 2.

As shown in FIG. 4 and FIG. 7A, the probe 27 is formed into a rod shape with, for example, a biocompatible metallic material (e.g. a titanium alloy). This probe 27 has a shaft (body portion) 51 extending in the shape of a rod. This shaft 51 has, on its distal side (distal portion), a treatment portion 52 in which a cutting blade protruding in the shape of a rake (in the shape of a hook) in a direction that intersects with the extending direction of the shaft 51 is formed, a back portion 53 flatly provided on the side opposite to the treatment portion 52 (the surface facing the treatment portion 52), and a pair of side portions 54 provided at positions between the treatment portion 52 and the back portion 53. The central axis C of the shaft 51 (the probe 27) is located at the position between the treatment portion 52 and the back portion 53. A proximal portion of the probe 27 (the shaft 51) is linked to the horn member 42. Thus, the probe 27 can conduct a treatment to transmit the ultrasonic vibration generated in the ultrasonic vibrator 41, and chip bones with the distal portion (the treatment portion 52) of the probe 27.

As shown in FIG. 2, the probe 27 is electrically connected to a first plug 46 provided in the holding portion 25. The first plug 46 is electrically connected to one end of one second electric wiring line 48a of two second electric wiring lines 48. The other end of this second electric wiring line 48a is electrically connected to a high-frequency electric current supply 47 of the electric supply unit 37. As a result, the probe 27 becomes one pole of a bipolar electrode to conduct a bipolar treatment. In the present embodiment, the second electric wiring line 48a is electrically connected to a negative pole of the high-frequency electric current supply 47. Thus, the probe 27 constitutes a return electrode in the bipolar treatment.

As shown in FIG. 4 and FIG. 7A, the sheath 28 has a circularly cylindrical body portion 55 fixed to the holding portion 25, a protrusion 56 which is provided on the distal side of the body portion 55 and which protrudes to cover the back portion 53 of the probe 27, and a cutout 57 which is made to expose the treatment portion 52 and the side portions 54 of the probe 27 to the external. This sheath 28 is made of an electrically conductive material such that the high-frequency electric current can be passed therethrough.

Figure 8:
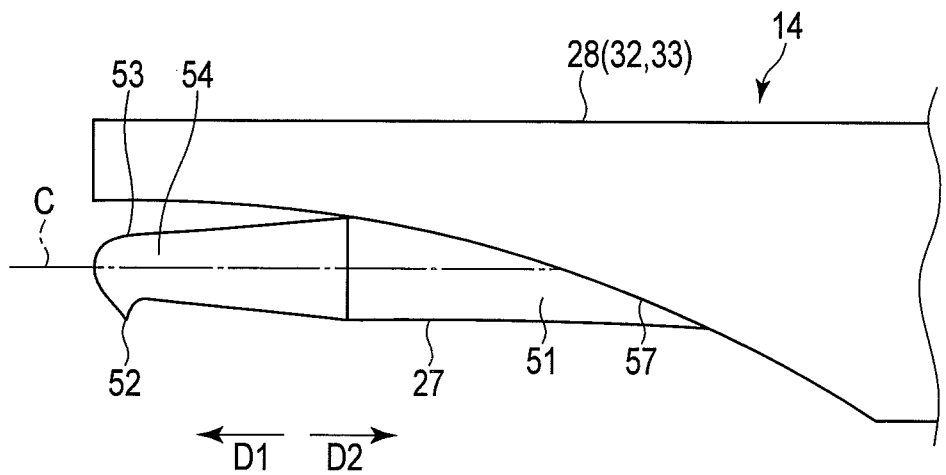
FIG. 8 is a side view showing the probe and the sheath shown in FIG. 7A from a lateral direction.

As shown in FIG. 7A and FIG. 8, the cutout 57 is formed obliquely to the extending direction of the probe 27, more specifically, is obliquely formed so that a part on the treatment portion 52 side of the probe 27 is chipped off toward the distal direction of the probe 27. To be more specific, the cutout 57 is formed to be curved convexly in a direction in which the back portion 53 of the probe 27 is present when seen from a side direction, as shown in FIG. 8. That is, the cutout 57 is oblique to the extending direction of the probe 27 on the proximal direction D2 side of the probe 27, but is in a direction substantially parallel to the extending direction of the probe 27 on the distal direction D1 side of the probe 27. As shown in FIG. 7A, in the present embodiment, the position of the distal end of the protrusion 56 of the sheath 28 corresponds to the position of the distal end of the probe 27.

As shown in FIG. 2, the sheath 28 is electrically connected to a second plug 58 provided in the holding portion 25. The second plug 58 is electrically connected to one end of the other second electric wiring line 48b of the two second electric wiring lines 48. The other end of this second electric wiring line 48b is electrically connected to the high-frequency electric current supply 47 of the electric supply unit 37. As a result, the sheath 28 becomes the other pole of the bipolar electrode to conduct the bipolar treatment. In the present embodiment, the second electric wiring line 48b is electrically connected to a positive pole of the high-frequency electric current supply 47. Thus, the sheath 28 constitutes an active electrode in the bipolar treatment.

As shown in FIG. 4 and FIG. 7A, the first insulating member 32 and the second insulating member 33 are attached to the sheath 28, or the sheath 28 is coated with the first insulating member 32 and the second insulating member 33. The first insulating member 32 and the second insulating member 33 are, for example, insulating tubes made of a synthetic resin material or coating films coated with an insulating member. In the present embodiment, the first insulating member 32 covers the inner peripheral surface of the sheath 28, and the second insulating member 33 covers the outer peripheral surface of the sheath 28. Consequently, the sheath 28 is in a state where an end face 56a of the protrusion 56 alone is exposed to the external. Thus, the end face 56a of the protrusion 56 as a partial region on the distal side of the sheath 28 functions as the other pole in the bipolar electrode. The high-frequency electric current then flows to the distal portion of the probe 27 from the end face 56a of the protrusion 56 to enable the bipolar treatment. In other words, the end face 56a of the protrusion 56 functions as the active electrode, and the distal portion of the probe 27 functions as the return electrode. In this way, the first insulating member 32 and the second insulating member 33 as the insulating members expose the partial region on the distal side of the sheath 28 alone to the external and cover other regions, whereby the bipolar treatment can be conducted between the partial region on the distal side of the sheath 28 and the distal portion of the probe 27.

As shown in FIG. 7B, a distal end face 56aa of the end face 56a alone may be exposed to the outside, and a side end face 56ab may be covered with the first insulating member 32 or the second insulating member 33. According to this structure, the high-frequency electric current can be concentrated in the distal end face 56aa during the bipolar treatment. This permits a treatment such as coagulation or blood stanching conducted by use of the bipolar treatment to be completed in a short time.

Figure 5:
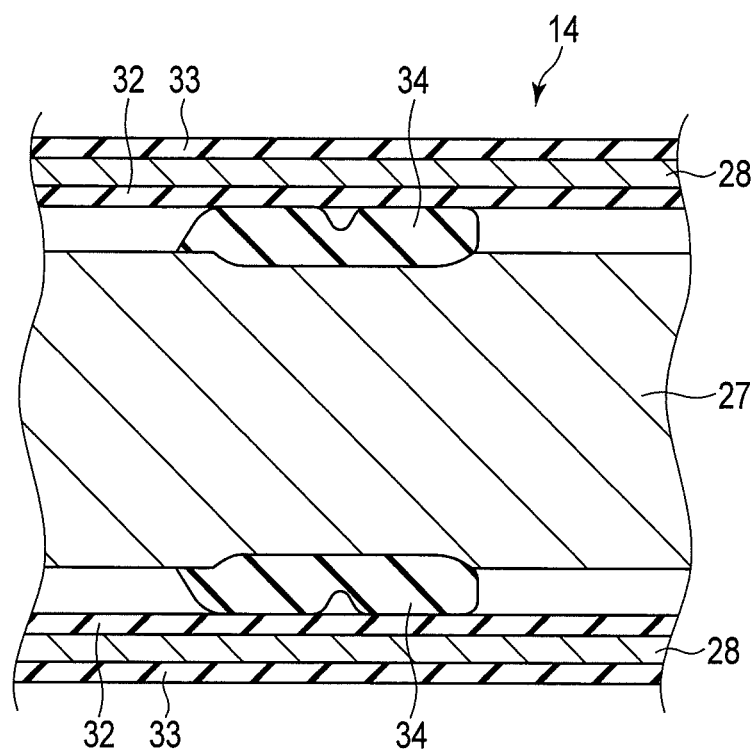
FIG. 5 is a sectional view showing the seal member shown in FIG. 4 in a magnified form.
Figure 6:
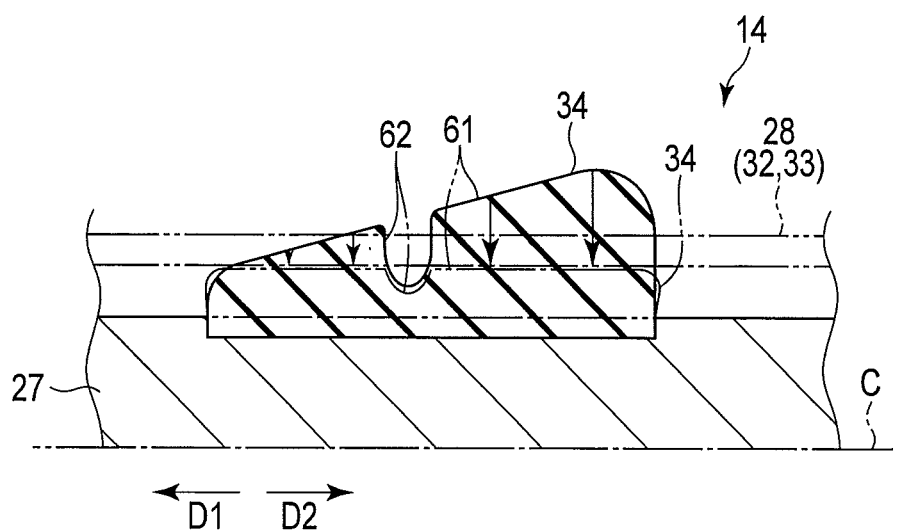
FIG. 6 is a sectional view showing a state (solid line) before the seal member shown in FIG. 5 is put in the sheath and a state (broken line) where the seal member is put in the sheath.

As shown in FIG. 5 and FIG. 6, the seal member 34 is disposed at the position of a node of the ultrasonic vibration transmitted to the probe 27, and is provided for the purpose of blocking any liquid from entering the proximal side of the probe 27. As shown in FIG. 5, the seal member 34 is ring-shaped by a rubber-like elastic resin (elastic body). As indicated by a solid line in FIG. 6, the seal member 34 becomes greater in thickness dimension in the radial direction of the probe 27 as the seal member 34 comes closer to the proximal direction D2 of the probe 27 in a state before the seal member 34 is put into the sheath 28. On the other hand, as indicated by a two-dot chain line in FIG. 6, the seal member 34 is compressed into a ring shape having a flat section in a state after the seal member 34 is put into the sheath 28. Thus, in the present embodiment, the pressure by which the seal member 34 is pressed to the sheath 28 and the first insulating member 32 is higher as the seal member 34 comes closer to the proximal side of the probe 27. Therefore, the seal member 34 according to the present embodiment has a structure that does not permit any liquid from entering the proximal side of the probe 27.

The seal member 34 has an abutment surface 61 which abuts on the first insulating member 32, and a slot 62 recessed from the abutment surface 61 in a direction in which the probe 27 is present. The slot 62 is provided at a substantially intermediate position in the extending direction of the probe 27 in the seal member 34. The slot 62 is formed to keep a predetermined space between the first insulating member 32 and the slot 62, and can retain therein a liquid which enters the space between the first insulating member 32 and the abutment surface 61. This prevents the liquid from entering the proximal side of the probe 27 from the seal member 34.

As shown in FIG. 1, the electric supply unit 37 has the ultrasonic electric current supply 45, the high-frequency electric current supply 47, and an energy controller 63 which controls the above. The energy controller 63 can control the supply of an ultrasonic generating electric current from the ultrasonic electric current supply 45 and the supply of the high-frequency electric current from the high-frequency electric current supply 47. When the first energy input buttons 35 are operated by the surgeon, the energy controller 63 supplies the ultrasonic generating electric current to the vibration generator 26 via the ultrasonic electric current supply 45. As a result, ultrasonic vibration is transmitted to the probe 27. When the second energy input button 38 is operated by the surgeon, the energy controller 63 supplies the high-frequency electric current to the sheath 28 via the high-frequency electric current supply 47.

Figure 9:
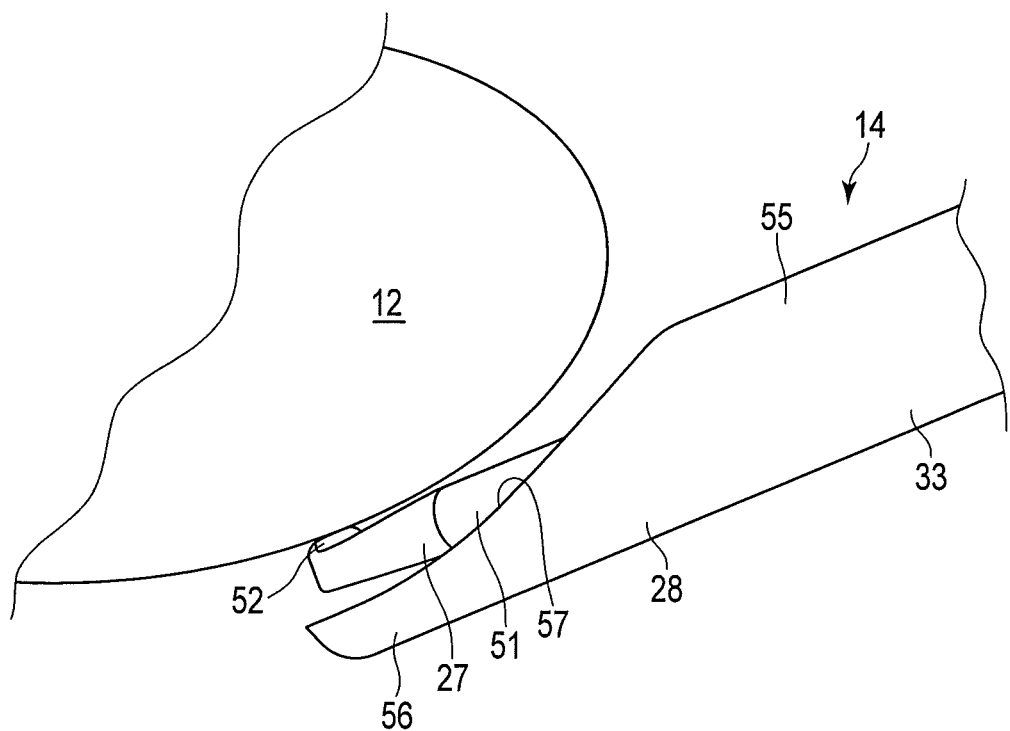
FIG. 9 is a perspective view showing a state where the treatment instrument shown in FIG. 1 is used to chip a bone.

Next, functions of the treatment system 11 (an arthroscopic surgical method using the treatment system 11)

according to the present embodiment are described with reference to FIG. 9 and FIG. 10. As shown in FIG. 1, the surgeon inserts the insertion portion 21 of the arthroscope 15 into the articular cavity 23. In a state where the surgeon observes with the arthroscope 15, the surgeon inserts the sheath 28 and the probe 27 of the treatment instrument 14 into the articular cavity 23. In this instance, the probe 27 which is ultrasonically vibrated can be used to remove a part of an articular capsule 23A around the articular cavity 23. Thus, the same probe 27 as that in a later-described treatment of the first bone 12 can be used, and it is not necessary to replace the treatment instrument 14. Before the treatment with the treatment instrument 14, the articular cavity 23 is filled with an arthroscopic perfusate comprising a lactate Ringer solution or an electrically conductive liquid 64 (electrolytic liquid) such as physiological saline by a known method.

As shown in FIG. 1, the sheath 28 and the probe 27 are inserted between the first bone 12, and the second bone 13 facing the first bone 12. As shown in FIG. 9, the treatment portion 52 of the probe 27 is brought into abutment with the treatment target first bone 12, and the surgeon operates the first energy input buttons 35, whereby ultrasonic vibration can be applied to the probe 27. Consequently, the probe 27 and the treatment portion 52 at its distal end ultrasonically vibrate. The surgeon can conduct a treatment to, for example, chip undesirable parts of the treatment target first bone 12 with the ultrasonically vibrating probe 27 while finely adjusting the positions and angles of the sheath 28 and the probe 27 (the treatment portion 52). This treatment includes various treatments to, for example, remove undesirable bone spurs present in the first bone 12 or tissues around the first bone 12.

In the case where a tissue including blood vessels (e.g. the first bone 12 and its surrounding tissues) bleeds when the surgeon treats this tissue, the surgeon can conduct a blood stanching treatment as needed. When conducting the blood stanching treatment, the surgeon brings the end face 56a of the protrusion 56 of the sheath 28 into abutment with a bleeding tissue T (e.g. the first bone 12 and its surrounding tissues), as shown in FIG. 10. In this state, if the surgeon operates the second energy input button 38, the high-frequency electric current is supplied from the end face of the end face 56a of the sheath 28, and this bleeding tissue can be cauterized. In the present embodiment, the high-frequency electric current concentrates because the end face 56a of the protrusion 56 of the sheath 28 alone is not covered with the first insulating member 32 and the second insulating member 33, so that the blood stanching treatment can be conducted for this bleeding tissue without any problem even under an environment filled with the electrically conductive liquid 64.

In the meantime, the high-frequency electric current supplied from the end face 56a of the protrusion 56 of the sheath 28 is collected by the probe 27 via the bones and the electrically conductive liquid 64 filling in the articular cavity 23. The high-frequency electric current collected by the probe 27 is returned to the high-frequency electric current supply 47.

In this way, the surgeon can use the same treatment instrument 14 to conduct the treatment to remove a tissue such as a bone and the blood stanching treatment in the case of bleeding. Thus, there is no time loss from the bleeding to the actual blood stanching treatment, and there is no situation where the surgeon loses sight of the bleeding part.

After the completion of the blood stanching, the surgeon can again remove undesirable parts of the first bone 12 and their surrounding tissues with the treatment portion 52 of the probe 27 as needed.

According to the first embodiment, a treatment instrument which is used under an environment filled with an electrically conductive liquid comprises a probe which has a distal portion to chip a treatment target part by ultrasonic vibration and which allows the distal portion to function as one pole in a bipolar electrode, a hollow sheath which surrounds the probe, and an insulating member which covers the sheath except for a partial region on the distal side of the sheath so that the partial region functions as the other pole in the bipolar electrode.

According to this structure, one treatment instrument 14 enables both a treatment to chip a tissue such as a bone and a blood stanching treatment in the case of bleeding in a tissue such as a bone. Therefore, as compared to the case where a treatment instrument for a treatment to chip bones is different from a treatment instrument for blood stanching, there is no need for work to replace the treatment instruments at the time of bleeding, and blood stanching work can be smoothly done. The surgeon does not lose sight of the bleeding part in the process of replacing the treatment instruments, and the part to which the high-frequency electric current is applied can be reduced to reduce damage caused to the tissues of a patient. Even in the case of bleeding, blood can be quickly stanched to reduce the total bleeding amount, and the psychological burden of the surgeon can be reduced. Surgery time can also be reduced.

The above insulating member comprises a first insulating member which covers the inner peripheral surface of the sheath, and a second insulating member which covers the outer peripheral surface of the sheath. This permits the sheath 28 to supply the high-frequency electric current from its end face (distal end face) to the bone. It is therefore possible to reduce the area of a part in which the sheath 28 is exposed, and increase the density of the high-frequency electric current to be input to a tissue such as a bone. This enables a satisfactory blood stanching capability even under the electrically conductive liquid 64.

Consequently, it is possible to provide the treatment instrument 14 which is easily used by the surgeon and which lessens the burden for the patient as well.

In this case, the probe 27 comprises the back portion 53 provided on the side opposite to the treatment portion 52, and the side portions 54 provided at the positions between the treatment portion 52 and the back portion 53. The sheath 28 has the protrusion 56 which protrudes to cover the back portion 53, and the cutout 57 which is made to expose the treatment portion 52 and the side portions 54 of the probe 27.

According to this configuration, when the treatment to chip a tissue such as a bone with the probe 27 is conducted, the sheath 28 does not interfere with this treatment. The sheath 28 is cut out on the treatment portion 52 side and the side portions 54 side of the probe 27. This allows the height dimension of the sheath 28 to be a substantially half height (i.e. a height between the protrusion 56 of the sheath 28 and the probe 27) on the distal side of the sheath 28. Thus, the treatment instrument 14 can access even narrow places inside tissues, so that it is possible to improve the convenience of the surgeon and reduce surgery time.

The ring-shaped seal member 34 is provided to intervene between the probe 27 and the first insulating member 32 and block the liquid 64 from entering the proximal side of the probe 27. According to this configuration, it is possible to prevent the liquid 64 from entering the proximal direction D2 side of the probe 27, and prevent the increase of a load applied when the probe 27 is ultrasonically vibrated. This can prevent the treatment instrument 14 from being broken by immersion into water. The seal member 34 can prevent direct contact between the probe 27 and the first insulating member 32. This can prevent the first insulating member 32 from being broken when ultrasonic vibration is output by the probe 27.

The seal member 34 has rubber-like elasticity, and becomes greater in thickness dimension in the radial direction of the probe 27 as the seal member 34 comes closer to the proximal side of the probe 27. According to this configuration, it is possible to improve the performance of putting in the probe 27 when the probe 27 covered with the seal member 34 is put into the hollow sheath 28. The seal member 34 is brought into closer contact with the sheath 28 and the first insulating member 32 by higher pressure as the seal member 34 comes closer to the proximal side of the probe 27, which enables a structure that does not permit the entry of the liquid 64 as the seal member 34 comes closer to the proximal direction D2 side of the probe 27. This can further improve the reliability of the treatment instrument 14.

The probe 27 collects the above high-frequency electric current applied to the aforementioned bone. According to this configuration, the sheath 28 and the probe 27 can be the two poles of the bipolar, and the high-frequency electric current can be concentrated around the sheath 28 and the probe 27. This makes it possible to reduce the time required for the blood stanching treatment, and reduce the output of the high-frequency electric current necessary for blood stanching to reduce the apparatus in size.

Next, a first modification of the treatment system according to the first embodiment is described with reference to FIG. 11. The first modification is different from the first embodiment in the shape of the protrusion 56 of the sheath 28, but is the same as the first embodiment in other parts. Therefore, parts different from those in the first embodiment are primarily described, and the same parts as those in the first embodiment are neither shown nor described.

The sheath 28 has the circularly cylindrical body portion 55 fixed to the holding portion 25, the protrusion 56 which is provided on the distal direction D1 side of the body portion 55 and which protrudes to cover the back portion 53 of the probe 27, and the cutout 57 which is made to expose the treatment portion 52 and the side portions 54 of the probe 27 to the external.

In the present modification, the cutout 57 is obliquely formed. More specifically, the cutout 57 is obliquely formed so that an angle θ formed by an angular portion located at the intersection of a plane A defined by the cutout 57 and a tangent B to the outer peripheral surface of the second insulating member 33 is an obtuse angle.

According to the present modification, the plane A defined by the cutout 57 is oblique to a radial direction R of the probe 27 so that the area of the end face of the sheath 28 exposed from the space between the first insulating member 32 and the second insulating member 33 increases. According to this configuration, it is possible to apply the high-frequency electric current to a tissue such as a bone via the exposed portion of the sheath 28 increased in area when the bone is bleeding. This can improve the convenience of the surgeon.

Figure 12:
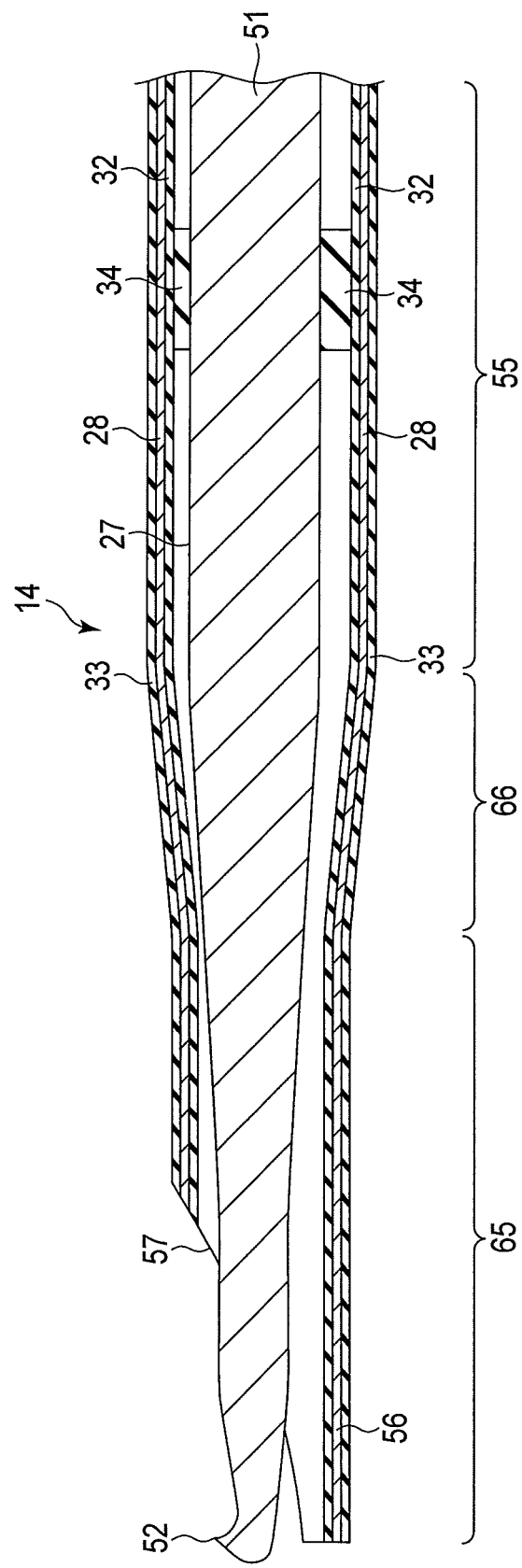
FIG. 12 is a sectional view showing the sheath and the probe according to a second modification of the first embodiment cut in a plane along the extending direction of the probe.

Next, a second modification of the treatment system according to the first embodiment is described with reference to FIG. 12. The second modification is different from the first embodiment in parts of the shape of the sheath 28, but is the same as the first embodiment in other parts. Therefore, parts different from those in the first embodiment are primarily described, and the same parts as those in the first embodiment are neither shown nor described.

The sheath 28 has the circularly cylindrical body portion 55 fixed to the holding portion 25, a small diameter portion 65 provided on the distal side of the body portion 55, and a narrow portion 66 which links the body portion 55 and the small diameter portion 65. The diameter of the small diameter portion 65 is smaller than the diameter of the body portion 55. It is preferable that the diameter of the small diameter portion 65 be suitably set within the range of half to ⅔ of the diameter of the body portion 55.

The small diameter portion 65 has the protrusion 56 which protrudes to cover the back portion 53 of the probe 27, and the cutout 57 which is made to expose the treatment portion 52 and the side portions 54 of the probe 27 to the external. The shapes of the protrusion 56 and the cutout 57 are similar to those in the first embodiment.

According to the second modification, the sheath 28 has the small diameter portion 65 which is provided on the distal direction D1 side and which is smaller in diameter than the part on the proximal direction D2 side, and the protrusion 56 and the cutout 57 are provided in this small diameter portion 65. According to this configuration, the height dimension in the distal portion of the sheath 28 (the height dimension between the protrusion 56 of the sheath 28 and the probe 27) can be smaller than in the first embodiment. Consequently, approachability of even narrow parts of tissues is improved, the convenience of the surgeon can be improved, and surgery time can be reduced.

Next, a third modification of the treatment system according to the first embodiment is described with reference to FIG. 13. The third modification is different from the first embodiment in parts of the shape of the seal member 34, but is the same as the first embodiment in other parts. Therefore, parts different from those in the first embodiment are primarily described, and the same parts as those in the first embodiment are neither shown nor described.

The seal member 34 is disposed at the node position of the ultrasonic vibration transmitted to the probe 27. The seal member 34 is ring-shaped by a rubber-like elastic resin (elastic body). The seal member 34 has the abutment surface 61 which abuts on the first insulating member 32, the slot 62 recessed from the abutment surface 61 to extend obliquely to the extending direction of the probe 27, and a sealing piece 67 which is provided at a position between the slot 62 and the first insulating member 32 and which defines part of the periphery of the slot 62. The slot 62 is provided at a substantially intermediate position in an extending direction L of the probe 27 in the seal member 34. The slot 62 is oblique to a direction to be closer to the central axis C of the probe 27 as the slot 62 comes closer to the proximal direction D2 side of the probe 27.

The sealing piece 67 forms an acute angle. The sealing piece 67 is pleat-shaped, and is pressed to the first insulating member 32 by pressure P which is part of the pressure of the liquid 64 that enters the slot 62. In this way, the sealing piece 67 acts like a valve to prevent the liquid 64 from entering the proximal side of the probe 27.

According to the third modification, the sealing piece 67 is provided, so that even when the treatment system 11 is used in the liquid 64, it is possible to prevent the liquid 64 from entering the proximal side of the probe 27. This can prevent the increase of a load causing a failure of the treatment instrument 14 when the ultrasonic vibration is transmitted to the probe 27.

Next, a fourth modification of the treatment system according to the first embodiment is described with reference to FIG. 14. The first modification is different from the first embodiment in parts of the shape of the seal member 34, but is the same as the first embodiment in other parts. Therefore, parts different from those in the first embodiment are primarily described, and the same parts as those in the first embodiment are neither shown nor described.

The seal member 34 is disposed at the position of the node of the ultrasonic vibration transmitted to the probe 27. The seal member 34 is ring-shaped by a rubber-like elastic resin (elastic body). The seal member 34 has the abutment surface 61 which abuts on the first insulating member 32, the slot 62 which is recessed from the abutment surface 61 and which helically extends around the probe 27, and a wall portion 68 which closes an end of the helical slot 62 on the proximal side of the probe 27.

According to the present modification, the slot 62 is helical, so that the volume of the slot 62 can be greater than the volume of the slot 62 in the first embodiment. Thus, the slot 62 can retain therein a greater amount of the liquid 64 than in the first embodiment even when the liquid 64 enters the space between the first insulating member 32 and the abutment surface 61. In addition, the wall portion 68 is provided, and therefore prevents the liquid 64 in the slot 62 from entering the proximal direction D2 side of the probe 27. This prevents the liquid 64 from entering the proximal side of the probe 27 and thus causing a failure of the treatment instrument 14.

[Second Embodiment]

A treatment system 11 according to a second embodiment is described with reference to FIG. 15 to FIG. 17. The treatment system. 11 according to the second embodiment is different from that according to the first embodiment in that a second cutout 71 is provided in the second insulating member 33, but is the same in other parts. Therefore, parts different from those in the first embodiment are primarily described, and the same parts as those in the first embodiment are neither shown nor described.

The treatment instrument 14 comprises the holding portion 25 which constitutes the outer envelope, the vibration generator 26 (transducer) housed in the holding portion 25, the rod-shaped probe 27 connected to the vibration generator 26, the hollow (circular cylindrical) sheath 28 which covers the periphery of the probe 27 to protect the probe 27, the knob 31 (rotational knob) rotatably fixed to the holding portion 25, the first insulating member 32 which covers the inner peripheral surface of the sheath 28, the second insulating member 33 which covers the outer peripheral surface of the sheath 28, the seal member 34 provided between the probe 27 and the first insulating member 32, and the energy input buttons 35 and 38 provided in the holding portion 25.

Figure 15:
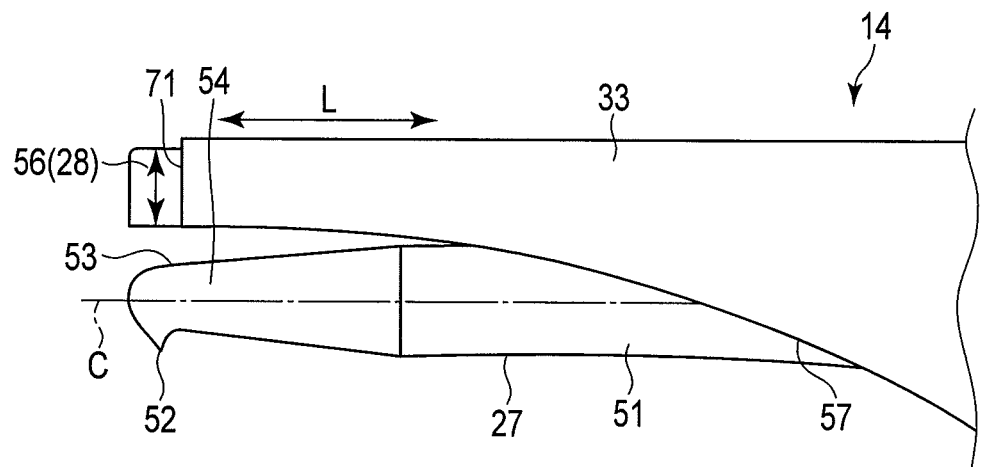
FIG. 15 is a side view showing the probe and the sheath of the treatment instrument of a treatment system according to a second embodiment.
Figure 16:
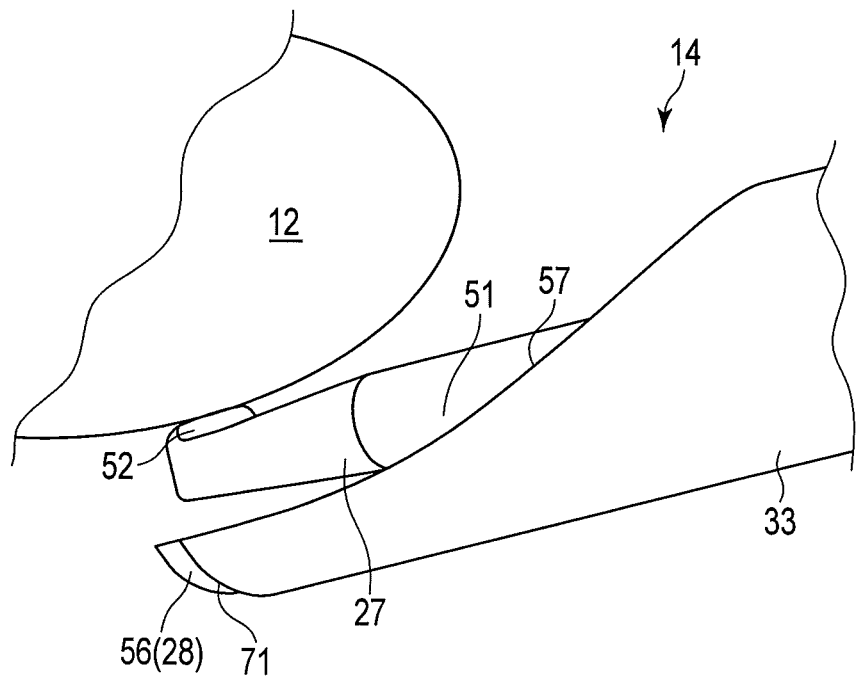
FIG. 16 is a perspective view showing a state where the treatment instrument shown in FIG. 15 is used to chip a bone.

As shown in FIG. 15, the second insulating member 33 has the second cutout 71. The second cutout 71 exposes the outer peripheral surface of the distal portion of the sheath 28 in a belt shape in a direction that intersects with the extending direction L of the sheath 28.

Next, functions of the treatment system 11 (the arthroscopic surgical method using the treatment system 11) according to the present embodiment are described with reference to FIG. 16 and FIG. 17.

As in a state shown in FIG. 1, the surgeon inserts the insertion portion 21 of the arthroscope 15 into the articular cavity 23. In a state where the surgeon observes with the arthroscope 15, the surgeon inserts the sheath 28 and the probe 27 of the treatment instrument 14 into the articular cavity 23. Before the treatment with the treatment instrument 14, the articular cavity 23 is filled with the arthroscopic perfusate comprising the lactate Ringer solution or the electrically conductive liquid 64 (electrolytic liquid) such as physiological saline by a known method.

As in the state shown in FIG. 1, the sheath 28 and the probe 27 are inserted between the first bone 12, and the second bone 13 facing the first bone 12. As shown in FIG. 16, the treatment portion 52 of the probe 27 is brought into abutment with the treatment target first bone 12, and the surgeon operates the first energy input buttons 35, whereby ultrasonic vibration can be applied to the probe 27. Consequently, the probe 27 ultrasonically vibrates, and the surgeon finely adjusts the position and angle of the probe 27 (the treatment portion 52) and can thus conduct a treatment to, for example, chip undesirable parts of the treatment target first bone 12. This treatment includes various treatments to, for example, remove undesirable bone spurs present in the first bone 12 or tissues around the first bone 12.

In the case where a tissue including blood vessels (e.g. the first bone 12 and its surrounding tissues) bleeds when the surgeon treats this tissue, the surgeon can conduct a blood stanching treatment as needed. When conducting the blood stanching treatment, the surgeon can rotate the angle of the sheath 28 around the central axis C by rotating the holding portion 25 around the central axis C. The surgeon then brings a part of the sheath 28 exposed by the second cutout 71 into abutment with the bleeding tissue T (e.g. the first bone 12 and its surrounding tissues), as shown in FIG. 17. In this state, if the surgeon operates the second energy input button 38, the high-frequency electric current is supplied from the part of the sheath 28 exposed by the second cutout 71, and this bleeding tissue T can be cauterized. This permits the blood from the bleeding tissue T to be stanched. In the meantime, the high-frequency electric current supplied from the end face of the protrusion 56 of the sheath 28 is collected by the probe 27 via the electrically conductive liquid 64 filling the bones and the articular cavity 23.

In this way, the surgeon can use the same treatment instrument 14 to conduct the treatment to remove a tissue such as a bone and the blood stanching treatment in the case of bleeding. Thus, there is no time loss from the bleeding to the actual blood stanching treatment, and there is no situation where the surgeon loses sight of the bleeding part.

After the completion of the blood stanching, the surgeon can again rotate the angle of the sheath 28 around the central axis C as needed, and remove undesirable parts of the first bone 12 and their surrounding tissues with the treatment portion 52 of the probe 27.

According to the present embodiment, the second insulating member 33 has the second cutout 71 which exposes part of the outer peripheral surface of the sheath 28. According to this configuration, the second cutout 71 allows the outer peripheral surface of the sheath 28 to easily abut on a bone and its surrounding tissues. Consequently, the surgeon can smoothly conduct the blood stanching treatment, the convenience of the surgeon can be improved, and surgery time can be reduced. Moreover, the blood stanching treatment can be efficiently conducted owing to the part of the sheath 28 exposed by the second cutout 71, so that the total input amount of the high-frequency electric current can be reduced to minimize damage caused to the tissues of the patient.

Next, a modification of the treatment system. 11 according to the second embodiment is described with reference to FIG. 18. The first modification is different from the first embodiment in the shape of the second cutout 71, but is the same as the first embodiment in other parts. Therefore, parts different from those in the first embodiment are primarily described, and the same parts as those in the first embodiment are neither shown nor described.

The second insulating member 33 has the second cutout 71. The second cutout 71 is substantially semicircular (substantially semielliptic). In other words, the second cutout 71 is arc-shaped. That is, the second cutout 71 can expose the outer peripheral surface of the distal portion of the sheath 28 in the substantially semicircular shape or arc-shape. In the present modification, the area of the second cutout 71 is smaller than in the second embodiment. Thus, the density of the high-frequency electric current applied to the tissue in the bleeding part is higher.

According to the present embodiment, the second cutout 71 is substantially semicircular. According to this configuration, the area of the part that exposes the outer peripheral surface of the sheath 28 can be minimized. Therefore, the density of the high-frequency electric current that can be applied to bones can be higher, and the surgeon can more smoothly conduct the blood stanching treatment. This can improve the convenience of the surgeon, and reduce surgery time. Moreover, the blood stanching treatment can be efficiently conducted owing to the high-density high-frequency electric current, so that the total input amount of the high-frequency electric current can be reduced to minimize damage caused to the tissues of the patient.

[Third Embodiment]

Figure 21:
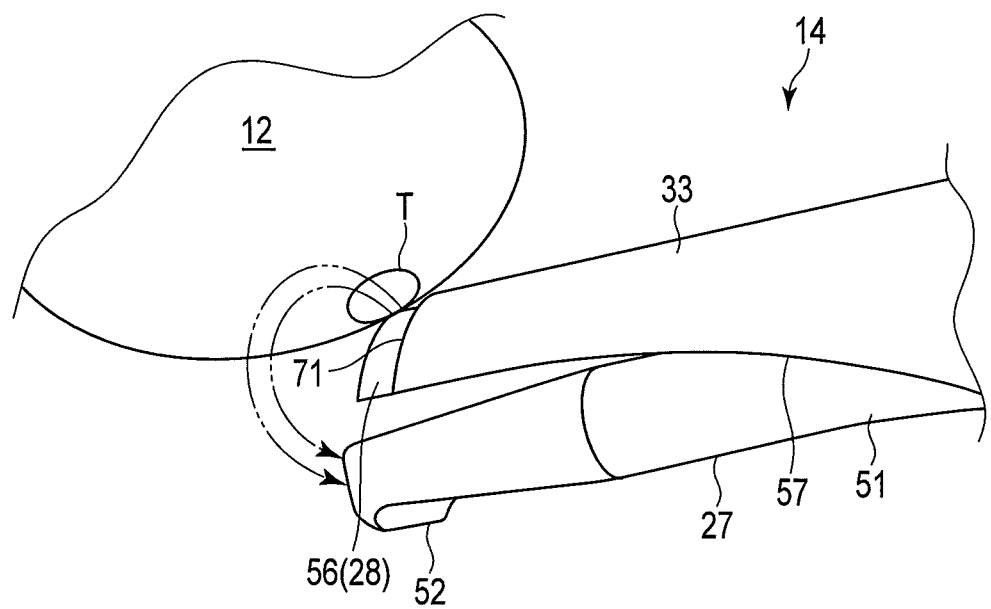
FIG. 21 is a perspective view showing a state where the treatment instrument shown in FIG. 19 is used to conduct a blood stanching treatment.

A treatment system 11 according to a third embodiment is described with reference to FIG. 19 to FIG. 21. The treatment system 11 according to the third embodiment is different from that according to the second embodiment in that the distal portion of the probe 27 protrudes more than the distal end of the protrusion 56 of the sheath 28, but is the same as the second embodiment in other parts. Therefore, parts different from those in the second embodiment are primarily described, and the same parts as those in the second embodiment are neither shown nor described.

In the present embodiment, the shape of the probe 27 and the shape of the sheath 28 are similar to those in the second embodiment.

As shown in FIG. 19, the distal portion of the probe 27 protrudes more than the distal end of the protrusion 56 of the sheath 28 in the extending direction L of the probe 27.

Next, functions of the treatment system 11 (the arthroscopic surgical method using the treatment system 11) according to the present embodiment are described with reference to FIG. 20 and FIG. 21.

The insertion method of the arthroscope 15 and the treatment instrument 14, and the method of filling the articular cavity 23 with the electrically conductive liquid 64 are similar to those in the second embodiment.

As shown in FIG. 20, the treatment portion 52 of the probe 27 is brought into abutment with the treatment target first bone 12, and the surgeon operates the first energy input buttons 35, whereby ultrasonic vibration can be applied to the probe 27. Consequently, the probe 27 ultrasonically vibrates, and the surgeon finely adjusts the position and angle of the ultrasonically vibrating probe 27 (the treatment portion 52) and can thus conduct a treatment to, for example, chip undesirable parts of the treatment target first bone 12. This treatment includes various treatments to, for example, remove undesirable bone spurs present in the first bone 12 or tissues around the first bone 12. In this instance, if the probe 27 protrudes more than the sheath 28 as in the present embodiment, the sheath 28 does not interfere during the treatment, and the undesirable parts of the first bone 12 are easily removed.

In the case where a tissue including blood vessels (e.g. the first bone 12 and its surrounding tissues) bleeds when the surgeon treats this tissue, the surgeon can conduct a blood stanching treatment as needed. When conducting the blood stanching treatment, the surgeon can rotate the angle of the sheath 28 around the central axis C by rotating the holding portion 25 around the central axis C. The surgeon then brings the part of the sheath 28 exposed by the second cutout 71 into abutment with the bleeding tissue T (e.g. the first bone 12 and its surrounding tissues), as shown in FIG. 21. In this state, if the surgeon operates the second energy input button 38, the high-frequency electric current is supplied from the part of the sheath 28 exposed by the second cutout 71, and this bleeding tissue can be cauterized. This permits the blood from the bleeding tissue T to be stanched. In the meantime, the high-frequency electric current supplied from the end face of the protrusion 56 of the sheath 28 is collected by the probe 27 via the electrically conductive liquid 64 filling the bones and the articular cavity 23.

According to the present embodiment, the distal portion of the probe 27 protrudes more than the distal end of the sheath 28. Thus, when the surgeon, for example, removes undesirable parts of a bone by the ultrasonic vibration of the probe 27, the sheath 28 does not interfere, and the treatment can be more easily conducted. Moreover, the visibility of the probe 27 can be satisfactory when a treatment to chip a tissue such as a bone with the probe 27 is conducted. This can improve the convenience of the surgeon when a treatment to chip a tissue such as a bone with the probe 27 is conducted.

[Fourth Embodiment]

A treatment system 11 according to a fourth embodiment is described with reference to FIG. 22 to FIG. 24. The treatment system 11 according to the fourth embodiment is different from that according to the second embodiment in that the distal end of the protrusion 56 of the sheath 28 protrudes more than the distal portion of the probe 27, but is the same as the second embodiment in other parts. Therefore, parts different from, those in the second embodiment are primarily described, and the same parts as those in the second embodiment are neither shown nor described.

In the present embodiment, the shape of the probe 27 and the shape of the sheath 28 are similar to those in the second embodiment.

Figure 22:
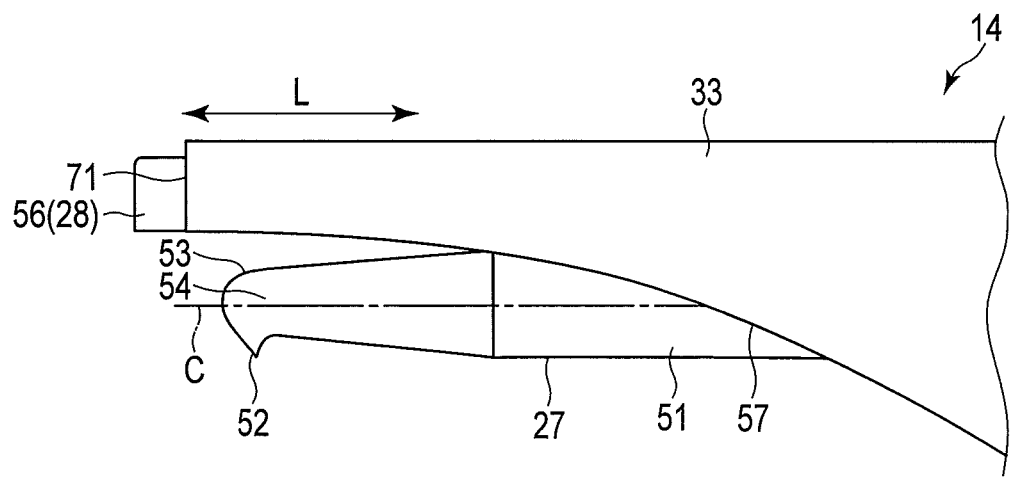
FIG. 22 is a side view showing parts in the vicinity of the probe and the distal portion of the sheath of the treatment portion of a treatment system according to a fourth embodiment.

As shown in FIG. 22, the distal end of the protrusion 56 of the sheath 28 protrudes more than the distal portion of the probe 27 in the extending direction L of the probe 27.

Next, functions of the treatment system 11 (the arthroscopic surgical method using the treatment system 11) according to the present embodiment are described with reference to FIG. 23 and FIG. 24.

The insertion method of the arthroscope 15 and the treatment instrument 14, and the method of filling the articular cavity 23 with the electrically conductive liquid 64 are similar to those in the second embodiment.

As shown in FIG. 23, the treatment portion 52 of the probe 27 is brought into abutment with the treatment target first bone 12, and the surgeon operates the first energy input buttons 35, whereby ultrasonic vibration can be applied to the probe 27. Consequently, the probe 27 ultrasonically vibrates, and the surgeon finely adjusts the position and angle of the ultrasonically vibrating probe 27 (the treatment portion 52) and can thus conduct a treatment to, for example, chip undesirable parts of the treatment target first bone 12. This treatment includes various treatments to, for example, remove undesirable bone spurs present in the first bone 12 or tissues around the first bone 12.

In the case where a tissue including blood vessels (e.g. the first bone 12 and its surrounding tissues) bleeds when the surgeon treats this tissue, the surgeon can conduct a blood stanching treatment as needed. When conducting the blood stanching treatment, the surgeon can rotate the angle of the sheath 28 around the central axis C by rotating the holding portion around the central axis C. The surgeon then brings the part of the sheath 28 exposed by the second cutout 71 into abutment with the bleeding tissue T (e.g. the first bone 12 and its surrounding tissues), as shown in FIG. 24. In this state, if the surgeon operates the second energy input button 38, the high-frequency electric current is supplied from the part of the sheath 28 exposed by the second cutout 71, and this bleeding tissue T can be cauterized. This permits the blood from the bleeding tissue to be stanched. In this instance, if the sheath 28 protrudes more than the probe 27 as in the present embodiment, the part of the sheath 28 exposed by the second cutout 71 is easily pressed to the bleeding part, and the blood stanching treatment can be more easily conducted. In the meantime, the high-frequency electric current supplied from the end face of the protrusion 56 of the sheath 28 is collected by the probe 27 via the electrically conductive liquid 64 filling the bones and the articular cavity 23.

According to the present embodiment, the distal end of the sheath 28 protrudes more than the distal end of the probe 27. According to this configuration, even in the case of bleeding when the treatment to chip a tissue such as a bone with the probe 27 is conducted, the work of pressing the part of the sheath 28 exposed by the second cutout 71 to the bleeding part can be more easily done. Consequently, the blood stanching work can be quickly done, and the convenience of the surgeon can be improved.

The present invention is not limited to the embodiments described above, and modifications may be suitably made without departing from the spirit thereof. The position of the distal portion of the probe 27 may be adjustable to the distal portion of the sheath 28 by the rotation of the knob 31 having a screw structure between the probe 27 and the knob 31. That is, according to such a structure, it is possible to move back the position of the distal portion of the probe 27 toward the proximal direction D2 side compared to the distal end of the sheath 28 by rotating the knob 31 clockwise around the central axis C of the probe 27, for example, when seen from the distal direction of the probe 27. In contrast, it is possible to move forward the probe 27 toward the distal direction D1 side compared to the distal end of the sheath 28 by rotating the knob 31 counterclockwise around the central axis C of the probe 27, for example, when seen from the distal direction of the probe 27. According to such a structure, the surgeon can suitably adjust the position of the probe 27 to the sheath 28 in accordance with the situation during surgery, and the convenience of the surgeon can be improved.

Furthermore, it is naturally also possible to combine the treatment systems 11 according to the respective embodiments described above into one treatment system.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument used under an environment filled with an electrically conductive liquid, the treatment instrument comprising:
   a probe that has a distal portion to chip a treatment target part by ultrasonic vibration, the distal portion of the probe functioning as a first pole in a bipolar electrode, the distal portion of the probe including:
      a treatment portion that contacts the treatment target part,
      a back portion provided on a side opposite to the treatment portion, and
      side portions provided at positions between the treatment portion and the back portion;
   a hollow sheath that surrounds the probe, the sheath including:
      a protrusion that protrudes to cover the back portion, and
      a cutout that exposes the treatment portion and the side portions of the probe; and
   an insulating member that covers the sheath except for a partial region on a distal side of the sheath, the partial region functioning as a second pole in the bipolar electrode, the insulating member includes a first insulating member that covers an inner peripheral surface of the sheath and a second insulating member that covers an outer peripheral surface of the sheath,
      wherein, when viewed in a cross-sectional view taken along an intersecting plane that intersects perpendicularly with an extending direction of the probe, an angle is formed by (i) a parallel line that is parallel with a plane defined by the cutout and (ii) a tangent line of an outer peripheral surface of the second insulating member at an intersection of the cutout and the outer peripheral surface of the second insulating member, and the angle formed by the parallel line and the tangent line is an obtuse angle.

2. The treatment instrument according to claim 1, the distal portion of the probe protrudes more than a distal end of the protrusion of the sheath in the extending direction of the probe.

3. The treatment instrument according to claim 1, a distal end of the protrusion of the sheath protrudes more than the distal portion of the probe in the extending direction of the probe.

4. The treatment instrument according to claim 1, further comprising a structure that is configured to adjust a position of the distal portion of the probe relative to a distal portion of the sheath.

5. The treatment instrument according to claim 1, wherein the second insulating member includes a second cutout that exposes part of the outer peripheral surface of the sheath.

6. The treatment instrument according to claim 1, further comprising a ring-shaped seal member that is located between the probe and the first insulating member, the ring-shaped seal member being configured to block the liquid from entering a proximal side of the probe.

7. The treatment instrument according to claim 6, wherein the seal member has rubber-like elasticity, and the seal member increases in thickness in a radial direction of the probe as the seal member extends closer to the proximal side of the probe.

8. The treatment instrument according to claim 6, wherein the seal member includes an abutment surface that abuts against the first insulating member, and a slot that is recessed from the abutment surface and is configured to retain in the slot the liquid that enters a space between the first insulating member and the abutment surface.

9. The treatment instrument according to claim 8, wherein:
   the slot extends obliquely in the extending direction of the probe, and
   the seal member includes a sealing piece, and the sealing piece defines part of a periphery of the slot and forms an acute angle at a position between the slot and the first insulating member.

10. The treatment instrument according to claim 8, wherein:
    the slot helically extends around the probe, and
    the seal member includes a wall portion, and the wall portion closes an end of the helical slot on the proximal side of the probe.

11. The treatment instrument according to claim 1, wherein:
    the sheath includes a small diameter portion that is located on a distal direction side and that is smaller in diameter than a part on a proximal direction side, and
    the protrusion and the cutout are located in the small diameter portion.

12. A treatment system comprising:
    the treatment instrument according to claim 1, and
    an endoscope apparatus to visualize a part to be treated with the treatment instrument.

\* \* \* \* \*